United States Patent

Hudetz et al.

[11] Patent Number: 5,962,371
[45] Date of Patent: Oct. 5, 1999

[54] HERBICIDAL COMPOSITION AND METHOD OF CONTROLLING WEEDS

[75] Inventors: Manfred Hudetz, Rheinfelden, Switzerland; Karl Gutbrod, Lörrach, Germany

[73] Assignee: Novartis Crop Protection, Inc., Greensboro, N.C.

[21] Appl. No.: 08/894,177

[22] PCT Filed: Jan. 31, 1996

[86] PCT No.: PCT/EP96/00398

§ 371 Date: Dec. 12, 1997

§ 102(e) Date: Dec. 12, 1997

[87] PCT Pub. No.: WO96/25043

PCT Pub. Date: Aug. 22, 1996

[30] Foreign Application Priority Data

Feb. 13, 1995 [CH]  Switzerland ............................. 421/95

[51] Int. Cl.[6] ........................... A01N 43/64; A01N 43/54
[52] U.S. Cl. ............................................ 504/135; 504/136
[58] Field of Search ..................... 504/116, 117, 504/136, 135

[56] References Cited

U.S. PATENT DOCUMENTS

| | | | |
|---|---|---|---|
| 4,478,635 | 10/1984 | Meyer et al. | 71/92 |
| 4,671,819 | 6/1987 | Meyer et al. | 71/93 |
| 5,209,771 | 5/1993 | Meyer | 504/178 |

FOREIGN PATENT DOCUMENTS

| | | |
|---|---|---|
| 2101489 | 1/1994 | Canada . |
| 0 318 276 | 5/1989 | European Pat. Off. . |
| 9007275 | 7/1990 | WIPO . |
| 92/08353 | 5/1992 | WIPO . |
| 93/25081 | 12/1993 | WIPO . |

OTHER PUBLICATIONS

Allen et al., The effect of DPX–5648 and glyphosate on roadside vegetation, Proc., South. Weed Sci. Soc., 35th (New Perspect. Wee Sci.), 258–63, 1982.
STN International, File CAPLUS 1991:223456

*Primary Examiner*—Jose G. Dees
*Assistant Examiner*—Alton Pryor
*Attorney, Agent, or Firm*—William A. Teoli, Jr.; John D. Peabody, III

[57] ABSTRACT

A herbicidal composition comprising at least one compound of formula I $$\text{(I)}$$

wherein $R_1$ is $-CO_2-\square-O$, $-CO_2CH_3$ or $-CH_2CH_2CF_3$, $R_2$ is methyl, methoxy or $-OCHF_2$,
$R_3$ is methyl or $-OCHF_2$ and
E is $=C-$ or $=N-$, with E being $=N-$ when $R_2$ is methoxy, or an agrochemically acceptable salt of at least one of the compounds of formula I, and a compound of formula II $$\text{(II)}$$

$$CH_3-\underset{\underset{OH}{|}}{\overset{\overset{O}{\|}}{P}}-CH_2CH_2-\underset{\underset{NH_2}{|}}{CH}-COOH$$

and/or of formula III $$\text{(III)}$$

$$HO-\underset{\underset{OH}{|}}{\overset{\overset{O}{\|}}{P}}-CH_2NHCH_2-COOH,$$

or an agrochemically acceptable salt of the compound of formula II and/or III, in admixture with one another.

12 Claims, No Drawings

HERBICIDAL COMPOSITION AND METHOD OF CONTROLLING WEEDS

This Appln is a 371 of PCT/EP96/00398 filed Jan. 31, 1996.

The present invention relates to a novel herbicidal composition comprising a herbicidal active ingredient combination that is suitable for the selective control of weeds in crops of useful plants, for example in crops of cereals, rape, sugar beet, sugar cane, plantation crops, rice, cotton and especially maize and soybeans.

The invention relates also to a method of controlling weeds in crops of useful plants and to the use of the novel composition for that purpose.

The compounds of formula I

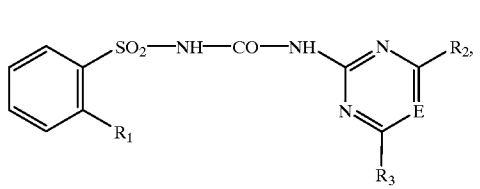

wherein $R_1$ is —$CO_2$—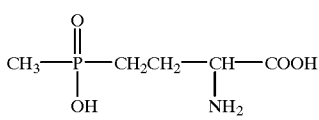,

—$CO_2CH_3$ or —$CH_2CH_2CF_3$, $R_2$ is methyl, methoxy or —$OCHF_2$,
$R_3$ is methyl or —$OCHF_2$ and
E is =CH— or =N—, with E being =N— when $R_2$ is methoxy, and salts thereof, have herbicidal action. This is described, for example, in EP-A-84 020, EP-A-496 701 and EP-A-120 814.

The following compounds of formulae II and III

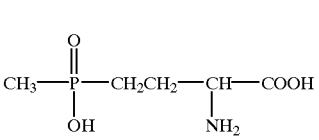

and

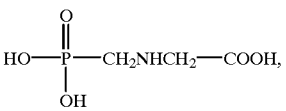

and their agrochemically acceptable salts, especially the alkali metal, ammonium and amine salts, are likewise known as herbicides(gluphosinates and glyphosates), for example in the "The Pesticide Manual", Tenth Edition 1994, Crop Protection Publications, and are also commercially available.

It has now surprisingly been found that a combination of variable proportions of at least one of the compounds of formula I with one of the above-mentioned compounds of formula II and/or III produces a herbicidal action that is capable of controlling the majority of the weeds that occur especially in crops of useful plants, pre-emergence and especially also post-emergence, without any significant damage being done to the useful plant.

There is therefore proposed in accordance with the present invention a novel composition for the selective control of weeds which, in addition to customary formulation adjuvants, comprises as active ingredient at least one compound of formula I

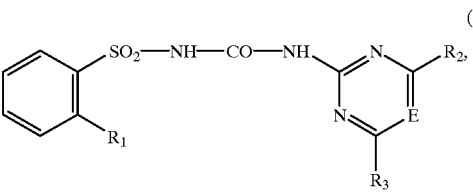

wherein $R_1$ is —$CO_2$—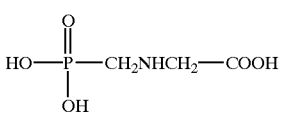,

—$CO_2CH_3$ or —$CH_2CH_2CF_3$, $R_2$ is methyl, methoxy or —$OCHF_2$, $R_3$ is methyl or —$OCHF_2$ and E is =CH— or =N—, with E being =N— when $R_2$ is methoxy, or an agrochemically acceptable salt of at least one of the compounds of formula I, and a compound of formula II $$CH_3 - \overset{O}{\underset{OH}{\overset{\|}{P}}} - CH_2CH_2 - \underset{NH_2}{\overset{}{CH}} - COOH \quad (II)$$

and/or of formula III $$HO - \overset{O}{\underset{OH}{\overset{\|}{P}}} - CH_2NHCH_2 - COOH, \quad (III)$$

or an agrochemically acceptable salt of the compound of formula II and/or III, in admixture with one another.

Examples of agrochemically acceptable salts of the compound of formula I are given in the afore-mentioned EP-A-84 020, EP-A-496 701 and EP-A-120 814, in each case on page 4. The amines described therein and also alkali metal hydroxides and ammonium hydroxide are likewise examples of suitable salt-forming agents for the compounds of formulae II and III.

The herbicide mixture according to the invention can be used against a large number of agronomically important weeds, such as Veronica, Galium, Papaver, Solanum, Chenopodium, Amaranthus, Xanthium, Abutilon, Ambrosia, Sagitaria, Ipomoea, Cassiastora, Datura stramonium, Sesbania exaltata and Sida spinosa, in crops of useful plants, especially in crops of maize and soybeans.

The compositions according to the invention are suitable for all methods of application customary in agriculture, for example pre-emergence application, post-emergence application, which is preferred, and seed dressing.

The herbicide mixture according to the invention is suitable especially for controlling weeds in crops of useful plants such as cereals, rape, sugar beet, sugar cane, plantation crops, rice, cotton and especially maize and soybeans.

Crops are to be understood as including those crops which have been made tolerant to herbicides or classes of herbicide, for example to glyphosates or gluphosinates, by conventional methods of breeding or gene technology.

The active ingredient combination according to the invention comprises the compound or compounds of formula I and the compound of formula II and/or III in any desired mixture ratio, generally with an excess of one component over the other. Preferred mixture ratios between the compound(s) of formula I and the mixing partner(s) of formula II and/or III are generally from 1:20 to 1:5.

The compositions according to the invention preferably comprise as compound of formula I a compound of formula Ia

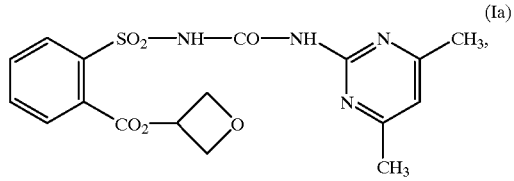

of formula Ib

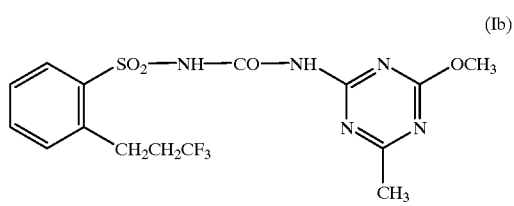

and/or formula Ic

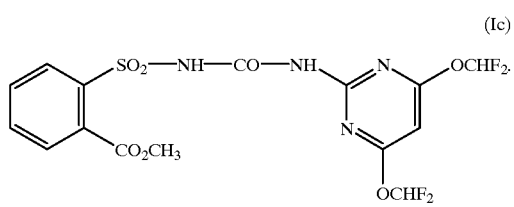

Other preferred compositions comprise a compound of formula Ia, Ib or Ic and the compound of formula II and/or III. Of those, compositions comprising a compound of formula Ia, Ib or Ic and the compound of formula II or III are especially suitable.

The rate of application may vary within wide limits and depends upon the nature of the soil, the type of use (pre- or post-emergence; seed dressing; application to the seed furrow; no tillage application, etc.), the crop plant, the weed to be controlled, the prevailing climatic conditions and other factors determined by the type of use, time of use and target crop. Generally the active ingredient mixture according to the invention can be applied at a rate of application of from 250 to 2500 g, especially from 500 to 1000 g, active ingredient mixture/ha.

In the composition according to the invention, the compound or compounds of formula I is/are present in a ratio by weight of from 1:100 to 1:0.001 with respect to the compound of formula II and/or III.

The mixtures of the compound or compounds of formula I with the compound of formula II and/or III may be used in unmodified form, that is to say as obtained in the synthesis, but they are preferably formulated in customary manner together with the adjuvants customarily employed in formulation technology e.g. into directly sprayable or dilutable solutions, dilute emulsions, wettable powders, soluble powders, dusts, granules or micro-capsules. As with the nature of the compositions, the methods of application, such as spraying, atomising, dusting, wetting, scattering or pouring, are chosen in accordance with the intended objectives and the prevailing circumstances.

The formulations, i.e. the compositions, preparations or mixtures comprising the compounds (active ingredients) of formulae I and II and/or III and, where appropriate, one or more solid or liquid formulation adjuvants, are prepared in a manner known per se, e.g. by homogeneously mixing and/or grinding the active ingredients with the formulation adjuvants, e.g. solvents or solid carriers. It is also possible to use surface-active compounds (surfactants) in the preparation of the formulations.

Suitable solvents are: aromatic hydrocarbons, preferably the fractions containing 8 to 12 carbon atoms, such as mixtures of alkylbenzenes, e.g. xylene mixtures or alkylated naphthalenes; aliphatic and cycloaliphatic hydrocarbons, such as paraffins, cyclohexane or tetrahydronaphthalene; alcohols, such as ethanol, propanol or butanol; glycols and their ethers and esters, such as propylene glycol or dipropylene glycol ether; ketones, such as cyclohexanone, isophorone or diacetone alcohol; strongly polar solvents, such as N-methyl-2-pyrrolidone, dimethyl sulfoxide or water; vegetable oils and esters thereof, such as rape oil, castor oil or soybean oil; and, where appropriate, also silicone oils.

The solid carriers used, e.g. for dusts and dispersible powders, are normally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite, and suitable nonsorbent carriers are, for example, calcite or sand. In addition, a great number of pregranulated materials of inorganic or organic nature can be used, e.g. especially dolomite or pulverised plant residues.

Depending upon the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Both water-soluble soaps and water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, synthetic surfactants are used, especially fatty alcohol sulfonates, fatty alcohol sulfates, sulfonated benzimidazole derivatives or alkylarylsulfonates.

The fatty alcohol sulfonates or sulfates are usually in the form of alkali metal salts, alkaline earth metal salts or unsubstituted or substituted ammonium salts and contain a $C_8$–$C_{22}$alkyl radical, which also includes the alkyl moiety of acyl radicals, e.g. the sodium or calcium salt of lignosulfonic acid, of dodecyl sulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain two sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 mol of ethylene oxide, or phospholipids.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Examples of non-ionic surfactants are nonylphenol polyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methyl sulfates or ethyl sulfates, e.g. stearyltrimethylammonium chloride or benzyldi(2-chloroethyl)ethylammonium bromide.

The surfactants customarily employed in formulation technology, which may also be used in the compositions according to the invention, are described inter alia in "Mc Cutcheon's Detergents and Emulsifiers Annual", MC Publishing Corp., Ridgewood, N.J., 1981; Stache, H., "Tensid-Taschenbuch" (Surfactant Handbook), Carl Hanser Verlag, Munich/Vienna 1981; and M. and J. Ash, "Encyclopedia of Surfactants", Vol. I-III, Chemical Publishing Co., New York, 1980–1981.

The herbicidal compositions usually comprise 0.1 to 99%, preferably 0.1 to 95%, of an active ingredient mixture of the compound(s) of formula I with the compound of formula II and/or III, 1 to 99% of a solid or liquid adjuvant, and 0 to 25%, preferably 0.1 to 25%, of a surfactant.

Whereas commercial products will preferably be formulated as concentrates, the end user will normally employ dilute formulations.

The compositions may also comprise further auxiliaries, such as stabilisers, e.g. vegetable oils or epoxidised vegetable oils (epoxidised coconut oil, rape oil or soybean oil), anti-foams, e.g. silicone oil, preservatives, viscosity regulators, binders and tackifiers, as well as fertilisers or other active ingredients.

Preferred formulations have especially the following composition (throughout, percentages are by weight):
Emulsifiable Concentrates
  active ingredient mixture: 1 to 90%, preferably 5 to 20%
  surface-active agent: 1 to 30%, preferably 10 to 20%
  liquid carrier: 5 to 94%, preferably 70 to 85%
Dusts
  active ingredient mixture: 0.1 to 10%, preferably 0.1 to 5% solid carrier: 99.9 to 90%, preferably 99.9 to 99%
Suspension Concentrates
  active ingredient mixture: 5 to 75%, preferably 10 to 50%
  water: 94 to 24%, preferably 88 to 30%
  surface-active agent: 1 to 40%, preferably 2 to 30%
Wettable Powders
  active ingredient mixture: 0.5 to 90%, preferably 1 to 80%
  surface-active agent: 0.5 to 20%, preferably 1 to 15%
  solid carrier: 5 to 95%, preferably 15 to 90%
Granules
  active ingredient mixture: 0.1 to 30%, preferably 0.1 to 15%
  solid carrier: 99.5 to 70%, preferably 97 to 85%

The following Examples further illustrate, but do not limit, the invention.

FORMULATION EXAMPLES

Mixtures of Compounds of Formulae I and II and/or III (Throughout, Percentages are by Weight)

| F1. Emulsifiable concentrates | a) | b) | c) | d) |
|---|---|---|---|---|
| mixture of compound(s) of formula I with one of the compounds of formula II and/or III | 5% | 10% | 25% | 50% |
| calcium dodecyl benzenesulfonate | 6% | 8% | 6% | 8% |
| castor oil polyglycol ether (36 mol of ethylene oxide) | 4% | — | 4% | 4% |
| octylphenol polyglycol ether (7–8 mol of ethylene oxide) | — | 4% | — | 2% |
| cyclohexanone | — | — | 10% | 20% |
| aromatic hydrocarbon mixture $C_9$–$C_{12}$ | 85% | 78% | 55% | 16% |

Emulsions of any desired concentration can be obtained from such concentrates by dilution with water.

| F2. Solutions | a) | b) | c) | d) |
|---|---|---|---|---|
| mixture of compound(s) of formula I with one of the compounds of formula II and/or III | 5% | 10% | 50% | 90% |
| 1-methoxy-3-(3-methoxy-propoxy)-propane | — | 20% | 20% | — |
| polyethylene glycol MW 400 | 20% | 10% | — | — |
| N-methyl-2-pyrrolidone | — | — | 30% | 10% |
| aromatic hydrocarbon mixture $C_9$–$C_{12}$ | 75% | 60% | — | — |

These solutions are suitable for application in the form of microdrops.

| F3. Wettable powders | a) | b) | c) | d) |
|---|---|---|---|---|
| mixture of compound(s) of formula I with one of the compounds of formula II and/or III | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7–8 mol of ethylene oxide) | — | 1% | 2% | — |
| highly dispersed silicic acid | 1% | 3% | 5% | 10% |
| kaolin | 88% | 62% | 35% | — |

The active ingredient is thoroughly mixed with the adjuvants and the mixture is thoroughly ground in a suitable mill, affording wettable powders which can be diluted with water to give suspensions of any desired concentration.

| F4. Coated granules | a) | b) | c) |
|---|---|---|---|
| mixture of compound(s) of formula I with one of the compounds of formula II and/or III | 0.1% | 5% | 15% |

-continued

| F4. Coated granules | a) | b) | c) |
|---|---|---|---|
| highly dispersed silicic acid | 0.9% | 2% | 2% |
| inorganic carrier (diameter 0.1–1 mm) for example CaCO₃ or SiO₂ | 99.0% | 93% | 83% |

The active ingredient is dissolved in methylene chloride and the solution is sprayed onto the carrier, and the solvent is subsequently evaporated off in vacuo.

| F5. Coated granules | a) | b) | c) |
|---|---|---|---|
| mixture of compound(s) of formula I with one of the compounds of formula II and/or III | 0.1% | 5% | 15% |
| polyethylene glycol MW 200 | 1.0% | 2% | 3% |
| highly dispersed silicic acid | 0.9% | 1% | 2% |
| inorganic carrier (diameter 0.1–1 mm) for example CaCO₃ or SiO₂ | 98.0% | 92% | 80% |

The finely ground active ingredient is uniformly applied, in a mixer, to the carrier moistened with polyethylene glycol. Non-dusty coated granules are obtained in this manner.

| F6. Extruder granules | a) | b) | c) | d) |
|---|---|---|---|---|
| mixture of compound(s) of formula I with one of the compounds of formula II and/or III | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants, and the mixture is moistened with water. The mixture is extruded and then dried in a stream of air.

| F7. Dusts | a) | b) | c) |
|---|---|---|---|
| mixture of compound(s) of formula I with one of the compounds of formula II and/or III | 0.1% | 1% | 5% |
| talcum | 39.9% | 49% | 35% |
| kaolin | 60.0% | 50% | 60% |

Ready-for-use dusts are obtained by mixing the active ingredient with the carriers, and grinding the mixture in a suitable mill.

| F8. Suspension concentrates | a) | b) | c) | d) |
|---|---|---|---|---|
| mixture of compound(s) of formula I with one of the compounds of formula II and/or III | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, giving a suspension concentrate from which suspensions of any desired concentration can be obtained by dilution with water.

It is often more practical for the compound(s) of formula I and the mixing partner of formula I and/or III to be formulated separately and to be brought together only shortly before application in the applicator in the desired mixture ratio in the form of a "tank mixture" in water.

BIOLOGICAL EXAMPLES

Example B1

Post-Emergence Test

In a greenhouse, monocotyledonous and dicotyledonous test plants are grown in plastic pots containing standard soil and in the 4- to 6-leaf stage are sprayed with an aqueous suspension of the test compounds of formula I, prepared from a 25% wettable powder formulation (Example F3, b)) corresponding to a rate of application of 2000 g a.i./ha (500 l water/ha). The test plants are then grown on in the greenhouse under optimum conditions. After about 18 days the test is evaluated in accordance with a scale of nine ratings (1=total damage, 9=no action). Ratings of from 1 to 4 (especially from 1 to 3) indicate a good to very good herbicidal action. In this test the compounds of formula I exhibit a strong herbicidal action. The same results are obtained when the compounds of formula I are formulated in accordance with Examples F1 and F2 and F4 to F8.

What is claimed is:

1. A herbicidal composition which comprises at least one compound of formula I

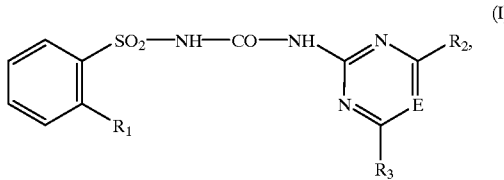

(I)

$R_2$ is methyl, methoxy or —OCHF₂, $R_3$ is methyl or —OCHF₂ and

E is =CH— or =N—, with E being =N— when $R_2$ is methoxy, or an agrochemically acceptable salt of at least one of the compounds of formula I, and a compound of formula II

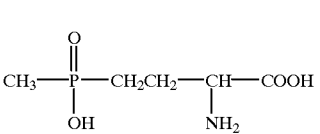

(II)

and/or of formula III

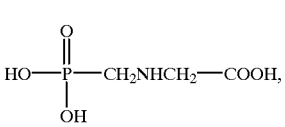

(III)

or an agrochemically acceptable salt of the compound of formula II and/or III, in admixture with one another with the exception of the compositions consisting essentially of a) 1-[(2-Methoxycarbonyl-phenyl)-sulfonyl]-3-[4,6-bis- (difluormethoxy)-pyrimidin-2-yl]-urea and a compound of formula II and/or III and b) 1-[(2-Methoxycarbonyl-phenyl)-sulfonyl]-3-[4-methoxy-6-methyl)-triazin-2-yl]-urea and a compound of formula II and/or III, and c) 1-[(2-Methoxycarbonyl-phenyl)-sulfonyl]-3-[4,6-(dimethyl)-pyrimidin-2-yl] urea and a compound of Formula II and/or III.

2. A composition according to claim 1 which comprises as compound of formula I a compound of formula Ia

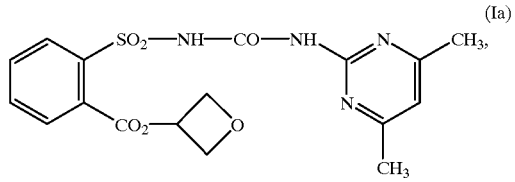

of formula Ib

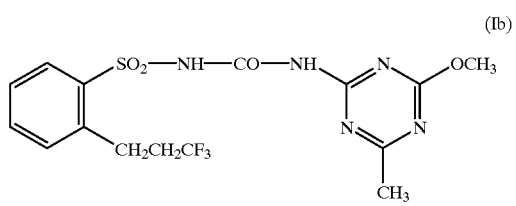

and/or formula Ic

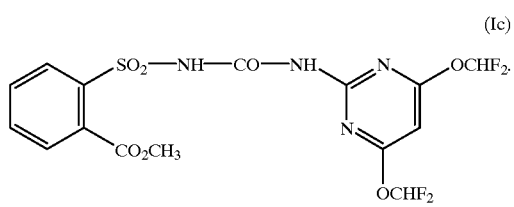

3. A herbicidal composition according to claim 1 which comprises a compound of formula Ia, Ib or Ic and the compound of formula II and/or III.

4. A herbicidal composition according to claim 3 which comprises a compound of formula Ia, Ib or Ic and the compound of formula II or III.

5. A herbicidal composition according to claim 1 which comprises the compound or compounds of formula I in a ratio by weight of from 1:100 to 1:0.001 with respect to the compound of formula II and/or III.

6. A method of controlling undesired plant growth in crops of useful plants, which comprises applying a herbicidally effective amount of a composition according to claim 1 to the cultivated plant or on the locus thereof.

7. A method according to claim 6 wherein the cultivated plant is maize or soybeans.

8. A method according to claim 6 wherein the cultivated plants are treated with the compositions at rates of application of a total amount of active ingredient of from 0.25 to 2.5 kg per hectare.

9. A composition according to claim 1 which comprises a compound of formula Ib

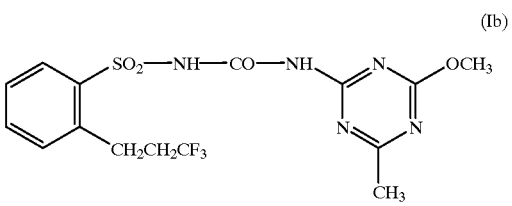

and/or formula Ic

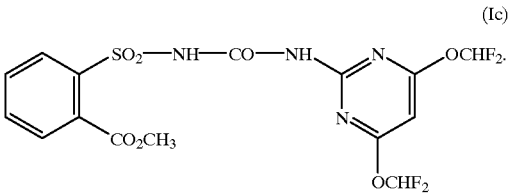

10. A herbicidal composition which comprises at least one compound of formula Ia

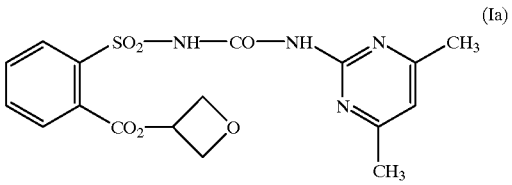

and a compound of formula II

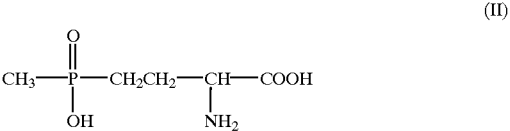

and/or of formula III

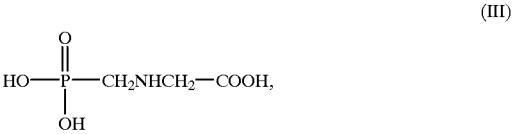

or an agrochemically acceptable salt of the compound of formula II and/or III; in admixture with one another, wherein the compound of formula Ia is in a ratio by weight of from 1:100 to 1:0.001 with respect to the compound of formula II and/or III.

11. A method of controlling undesired plant growth in crops of maize or soybeans, which comprises applying a herbicidally effective amount of a composition according to claim 10 to the cultivated plant or on the locus thereof.

12. A method according to claim 11 wherein the cultivated plants are treated with the compositions at rates of application of a total amount of active ingredient of from 0.25 to 2.5 kg per hectare.

* * * * *